United States Patent
Drèze et al.

(10) Patent No.: US 9,890,431 B2
(45) Date of Patent: Feb. 13, 2018

(54) STREPTOCOCCUS PNEUMONIAE DETECTION IN BLOOD

(75) Inventors: Pierre-Alexandre Drèze, Huy (BE); Pierre Smeesters, Kraainem (BE); Lena Demazy, Luttre (BE); Laurence Van Melderen, Waterloo (BE)

(73) Assignee: UNIVERSITÉ LIBRE DE BRUXELLES, Brussels (BE)

( * ) Notice: Subject to any disclaimer, the term of this patent is extended or adjusted under 35 U.S.C. 154(b) by 489 days.

(21) Appl. No.: 14/356,465

(22) PCT Filed: Nov. 15, 2011

(86) PCT No.: PCT/EP2011/070127
§ 371 (c)(1),
(2), (4) Date: May 6, 2014

(87) PCT Pub. No.: WO2013/071954
PCT Pub. Date: May 23, 2013

(65) Prior Publication Data
US 2014/0363814 A1    Dec. 11, 2014

(51) Int. Cl.
*C12Q 1/68* (2006.01)
*C12P 19/34* (2006.01)

(52) U.S. Cl.
CPC ........... *C12Q 1/689* (2013.01); *C12Q 1/6806* (2013.01); *C12Q 1/6816* (2013.01); *C12Q 2600/112* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,427,930 A | 6/1995 | Birkenmeyer et al. | |
| 5,541,308 A * | 7/1996 | Hogan ................. | C12Q 1/6811 435/6.12 |
| 5,744,311 A | 4/1998 | Fraiser et al. | |
| 5,866,366 A | 2/1999 | Kallender | |
| 6,025,134 A | 2/2000 | Sooknanan | |
| 6,027,889 A | 2/2000 | Barany et al. | |
| 6,033,881 A | 3/2000 | Himmler et al. | |
| 7,476,733 B2 | 1/2009 | Carvalho et al. | |
| 2006/0286552 A1 | 12/2006 | Goldsmith et al. | |
| 2007/0021373 A1* | 1/2007 | Doucette-Stamm ........................ | A61K 31/7052 514/44 R |
| 2007/0048758 A1* | 3/2007 | Lokhov ................. | C12P 19/34 435/6.12 |
| 2010/0234245 A1 | 9/2010 | McGee et al. | |

FOREIGN PATENT DOCUMENTS

| EP | 320308 A | 6/1989 |
|---|---|---|
| WO | WO 90/01069 A1 | 2/1990 |
| WO | WO 2004/090159 | 10/2004 |
| WO | WO 2005/103252 | 11/2005 |
| WO | WO 2006/020579 | 2/2006 |
| WO | WO 2007/056463 A2 | 5/2007 |
| WO | WO 2007/106407 | 9/2007 |

OTHER PUBLICATIONS van Haeften (Diagnostic Microbiology and Inf. Disease, 2003, vol. 47, pp. 407-414).*
Buck et al (Biotechniques (1999) 27(3):528-536).*
Chen (PLOs One, 2008, vol. 3, e2950, pp. 1-9).*
Arbique et al., "Accuracy of Phenotypic and Genotypic Testing for Identification of *Streptococcus pneumoniae* and Description of *Streptococcus pseudopneumoniae* sp. nov.," *J. Clin. Microbiol.*, vol. 42(10), pp. 4686-4696 (Oct. 2004).
Chalasani et al., "Clinical Utility of Blood Cultures in Adult Patients With Community-Acquired Pneumonia Without Defined Underlying Risks," *Chest*, Clinical Investigations, vol. 108(4), pp. 932-936 (Oct. 1995).
Grace et al., "Usefulness of Blood Culture for Hospitalized Patients Who Are Receiving Antibiotic Therapy," *Clin Infect Dis.*, Brief Reports, vol. 32, pp. 1651-1655 (Jun. 1, 2001).
Innings et al., "Identification of 43 *Streptococcus* Species by Pyrosequencing Analysis of the rnpB Gene," *J Clin Microbiol.*, vol. 43(12), pp. 5983-5991 (Dec. 2005).
Lehmann et al., "A multiplex real-time PCR assay for rapid detection and differentiation of 25 bacterial and fungal pathogens from whole blood samples," *Med Microbiol Immunol*, vol. 197, pp. 313-324 (2008).
International Search Report and Written Opinion of the International Searching Authority for International Application No. PCT/EP2011/070127.
Afonina et al., "Primers with 5' flaps improve real-time PCR," *BioTechniques*, vol. 43(6), pp. 770-774 (Dec. 2007).
Mahdi et al., "Pneumococcal Virulence Gene Expression and Host Cytokine Profiles during Pathogenesis of Invasive Disease," *Infection and Immunity*, vol. 76(2), pp. 645-657 (Feb. 2008); Epub Nov. 26, 2007.
Ogunniyi et al, "The genes encoding virulence-associated proteins and the capsule of *Streptococcus pneumoniae* are upregulated and differentially expressed in vivo," *Microbiology*, vol. 148 (7), pp. 2046-2053 (2002).
Park et al., "Identification of the cpsA gene as a specific marker for the discrimination of *Streptococcus pneumoniae* from viridans group *Streptococci*," Journal of Medical Microbiology, vol. 59(10), pp. 1146-1152 (2010); Epub Jul. 8, 2010.

* cited by examiner

*Primary Examiner* — Sarae Bausch
(74) *Attorney, Agent, or Firm* — Knobbe, Martens, Olson & Bear, LLP

(57) ABSTRACT

The present invention provides a method and a kit for detecting a *S. pneumoniae* nucleic acid in a sample. The method comprises the steps of isolating said nucleic acid and detecting hybridization between the *S. pneumoniae* nucleic acid and a labeled probe, wherein the detection of hybridization comprises detecting a change in signal from the labeled probe during or after hybridization relative to the labeled probe signal before hybridization. The method of the present invention is characterized in that said nucleic acid is a ribonucleic acid, which isolation comprises the addition of acidic phenol to said sample and the purification of said ribonucleic acid.

6 Claims, 1 Drawing Sheet

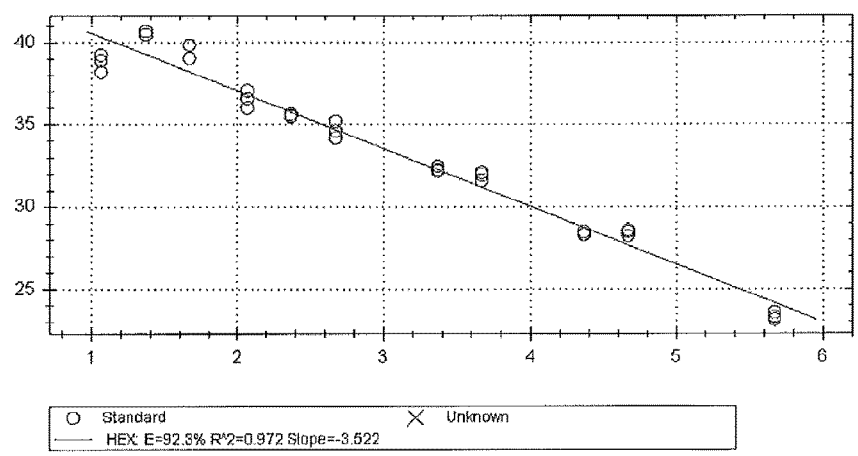

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
acgtctaaga atcagtcttt c                                            21

<210> SEQ ID NO 2
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 2
gacaccgaac taatagg                                                 17

<210> SEQ ID NO 3
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 3
taacagctac caacgacag                                               19

<210> SEQ ID NO 4
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 4
gcaagaagag tgggattatt c                                            21

<210> SEQ ID NO 5
<211> LENGTH: 12
<212> TYPE: DNA
<213> ORGANISM: Artificial Sequence
<220> FEATURE:
<223> OTHER INFORMATION: Chemically Synthesized

<400> SEQUENCE: 5
aataaatcat aa                                                      12

<210> SEQ ID NO 6

```
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 6
aataaatcat aaacgtctaa gaatcagtct ttc                         33

<210> SEQ ID NO 7
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 7
aataaatcat aacgacaccg aactaatagg                             30

<210> SEQ ID NO 8
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 8
aataaatcat aataacagct accaacgaca g                           31

<210> SEQ ID NO 9
<211> LENGTH: 33
<212> TYPE: DNA
<213> ORGANISM: Artificial Sequence
<220> FEATURE:
<223> OTHER INFORMATION: Chemically Synthesized

<400> SEQUENCE: 9
aataaatcat aagcaagaag agtgggatta ttc                         33

<210> SEQ ID NO 10
<211> LENGTH: 19
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)...(1)
<223> OTHER INFORMATION: A fluorophore HEX is covalently attached to the
      first nucleic acid
<220> FEATURE:
<221> NAME/KEY: misc_feature
<222> LOCATION: (19)...(19)
<223> OTHER INFORMATION: Quencher BHQ1 is covalently attached to the
      last nucleic acid

<400> SEQUENCE: 10
ccataggtgt caattccac                                         19

<210> SEQ ID NO 11
<211> LENGTH: 19
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)...(1)
<223> OTHER INFORMATION: A fluorophore FAM is covalently attached to the
```

```
      first nucleic acid
<220> FEATURE:
<221> NAME/KEY: misc_feature
<222> LOCATION: (19)...(19)
<223> OTHER INFORMATION: Quencher BHQ1 is covalently attached to the
      last nucleic acid

<400> SEQUENCE: 11
aaggtctcat ccactacga                                                    19

<210> SEQ ID NO 12
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 12
ccatctggct ctactgtg                                                     18

<210> SEQ ID NO 13
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 13
ggaacaggct ggtactac                                                     18

<210> SEQ ID NO 14
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 14
aataaatcat aaccatctgg ctctactgtg                                        30

<210> SEQ ID NO 15
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 15
aataaatcat aaggaacagg ctggtactac                                        30

<210> SEQ ID NO 16
<211> LENGTH: 16
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)...(1)
<223> OTHER INFORMATION: A fluorophore Texas-Red is covalently attached
      to the first nucleic acid
```

```
<220> FEATURE:
<221> NAME/KEY: misc_feature
<222> LOCATION: (16)...(16)
<223> OTHER INFORMATION: Quencher BHQ2 is covalently attached to the
      last nucleic acid

<400> SEQUENCE: 16
tgccagtgtt ccgtct                                                        16
```

STREPTOCOCCUS PNEUMONIAE DETECTION IN BLOOD

CROSS-REFERENCE TO RELATED APPLICATIONS

This application is the U.S. National Phase under 35 U.S.C. § 371 of International Application PCT/EP2011/070127, filed Nov. 15, 2011.

REFERENCE TO SEQUENCE LISTING

This application incorporates by reference the sequence listing submitted as ASCII text filed via EFS-Web on Aug. 27, 2014. The Sequence Listing is provided as a file entitled "SEQLIST_BAP41001_REV_082614," created on Aug. 26, 2014, and which is approximately 4 kilobytes in size.

FIELD OF THE INVENTION

The present invention relates to primers and probes for the detection Streptococcus pneumoniae, as well as kits including the probes and primers and methods of using the probes and primers. The invention further relates to a device for the detection of Streptococcus pneumonia.

BACKGROUND

Streptococcus pneumoniae (S. pneumoniae) is the chief cause of community-acquired pneumonia (CAP). S. pneumoniae is a Gram-positive bacteria responsible for considerable morbidity and mortality, causing diseases such as pneumonia, bacteremia, meningitis, acute otitis media, and sinusitis. It is estimated that 20% of S. pneumoniae cases lead to bacteremia, and other manifestations such as meningitis, with a mortality rate close to 30% even with antibiotic treatment. S. pneumoniae is found in the nasopharynx of 11-76% of the population, averaging 40-50% for children and 20-30% for adults (Ghaffar et al., J. Infect. Dis. 18, 638-646, 1999).

Those most commonly at risk for pneumococcal infection are children between 6 months and 4 years of age and adults over 60 years of age. Virtually every child will experience pneumococcal otitis media before the age of 5 years. It is estimated that 25% of all community-acquired pneumonia is due to pneumococcus (1,000 per 100,000 inhabitants). Recently, epidemics of disease have reappeared in settings such as chronic care facilities, military camps, and day care centers, a situation not recognized since the pre-antibiotic era. S. pneumoniae remains a significant human pathogen because of the morbidity and mortality it causes in young children, the elderly and in immune-compromised patients.

Amongst the diagnostic methods of pneumococcal pneumonia, bronchoalveolar lavage (BAL) or transthoracic needle aspiration are considered to be reliable, but they are invasive and cannot be performed routinely.

Identification of the bacterium in blood culture provides a definite diagnosis and can serve as an indicator of disease severity. However, the positivity rate of blood cultures rarely exceeds 10% in CAP (Chalasani et al., Chest., 108, 932-936, 1995), and can be below 1% if blood samples are obtained during antimicrobial treatment (Grace et al., Clin Infect Dis., 32, 1651-1655, 2001). Diagnosis of pneumococcal pneumonia is hindered by the lack of a highly sensitive and specific 'gold standard' method. Culture of sputum and nasopharyngeal secretions is controversial due to respiratory tract carriage of pneumococci. The limitations of culture based, conventional S. pneumoniae diagnostic tests make definitive diagnosis difficult to establish. For example, the isolation of S. pneumoniae from blood, the recognized definitive test for the presence of S. pneumoniae may lack sensitivity, only giving positive results in 20-30% of adult cases of pneumococcal pneumonia and less than 10% of children's cases. Serologic assays for both antibody and antigen detection suffer from a lack of specificity and sensitivity, for example the recently introduced urine antigen test, Binax NOW®, while shown to be sensitive and specific for adults by some studies, is unable to distinguish between carriage and disease in children.

Attempts to develop accurate diagnosis and assays were made leading to an increase, in clinical practice, of the use of polymerase chain reaction (PCR) protocols to detect bacteria in blood samples. Commercial PCR procedures applied to blood samples, use conserved PCR targets for genes that are common to all bacteria. This is a promising strategy for pathogens like Staphylococcus aureus and Gram-negative enteric bacilli, but not for S. pneumoniae. It is difficult for PCR against common bacterial genes to distinguish between S. pneumoniae and alpha-haemolytic streptococci, as they are closely related (Innings et al., J Clin Microbiol. 43, 5983-5991, 2005 and Lehmann et al., Med Microbiol Immunol. 197, 313-324, 2008).

In addition, the misidentification of pneumococcus-like viridans Streptococci (P-LVS) as S. pneumoniae presents additional opportunities for misdiagnosis especially when attempted with non-sterile site specimens such as sputum. Identification of S. pneumoniae has typically been based on bile solubility, optochin sensitivity, and GenProbe ACCUPROBE® Pneumococcus identification test; but increasingly there have been reports of P-LVS isolated from clinical specimens, which may give positive or variable reactions in one or more of these standard pneumococcal tests. Among a subset of reported isolates of P-LVS, a newly recognized species, classified as S. pseudopneumoniae (Spseudo), has been described and characterized (Arbique et al., J. Clin. Microbiol. 42, 4686-4696, 2004). Spseudo organisms are bile solubility negative and resistant to optochin in the presence of 5% $CO_2$, but are ACCUPROBE® positive (Arbique et al., J. Clin. Microbiol. 42, 4686-4696, 2004) and thus yield a false positive for S. pneumoniae infection. The appearance of these pneumococcus-like organisms has complicated identification and diagnosis even further, especially when non-sterile site respiratory specimens are used for making determinations.

U.S. Pat. No. 7,476,733 discloses a real-time PCR method for detection of the pneumococcal surface adhesion protein (psaA) gene. Patent application US 2010/0234245 provides methods for diagnosing an S. pneumoniae infection by analyzing a biological specimen from a subject to detect a broad variety of S. pneumoniae nucleic acids, such as S. pneumoniae lytA, ply, and psaA nucleic acids.

One of the major drawbacks of the methods described in the prior art is that they target the S. pneumoniae DNA. This drawback is due to the fact that S. pneumonia usually establishes an obligate asymptomatic association within the human nasopharyngeal cavity. This asymptomatic association leads to false positives when the pneumonia is caused by an organism different than S. pneumonia. Therefore, the need exists for diagnostic methods and assays allowing the detection of the presence and the activity of S. pneumoniae.

The aim of the present invention is to provide a solution and to overcome the above mentioned disadvantage. An object of the invention is to propose a diagnostic method wherein the targeted nucleic acid is the RNA of S. pneumo-

SUMMARY

In a first aspect, the present invention provides a method for detecting a *S. pneumoniae* nucleic acid in a sample. The method comprises the steps of isolating said nucleic acid and detecting hybridization between the *S. pneumoniae* nucleic acid and a labeled probe, wherein the detection of hybridization comprises detecting a change in signal from the labeled probe during or after hybridization relative to the labeled probe signal before hybridization. The method is characterized in that said nucleic acid is a ribonucleic acid, which isolation comprises the addition of acidic phenol to said sample and the purification of said ribonucleic acid (RNA). The detection of RNA instead of DNA is advantageous as it allows the selective detection of the actively replicating bacteria responsible for pneumococcal infection.

In a preferred embodiment, the method of the present invention further comprises the steps of synthesizing a deoxyribonucleic acid from the isolated ribonucleic acid; contacting said deoxyribonucleic acid with at least one primer; contacting said deoxyribonucleic acid with at least one labeled probe and amplifying the *S. pneumoniae* deoxyribonucleic acid by a method selected from the group of polymerase chain reaction (PCR), reverse transcriptase-polymerase chain reaction (RT-PCR), real-time reverse transcriptase-polymerase chain reaction (rt RT-PCR), ligase chain reaction, or transcription-mediated amplification (TMA), preferably by real-time PCR.

In a preferred embodiment, the present invention provides a method wherein said at least one primer have a length comprised between 15 and 40 nucleotides capable of hybridizing under very high stringency conditions to a *S. pneumoniae* ribonucleic acid.

In a preferred embodiment, the present invention provides a method wherein the primer comprises a nucleic acid sequence at least 90%, preferably 95%, more preferably 100% identical to the nucleotide sequence set forth as SEQ ID NO: 1, SEQ ID NO: 2, SEQ ID NO: 3 or SEQ ID NO: 4.

In a preferred embodiment, the present invention provides a method wherein said at least one primer comprises at least one flap sequence, which is at least 90%, preferably 95%, more preferably 100% identical to the nucleotide sequence set forth as SEQ ID NO: 5. Use of primers having flap sequences is advantageous as it leads to an increase of real-time PCR fluorescent signal.

In a preferred embodiment, the present invention provides a method wherein the labeled probe is radiolabeled, fluorescently-labeled, biotin-labeled, enzymatically-labeled, or chemically-labeled.

In a preferred embodiment, the present invention provides a method wherein the probe is labeled with a fluorophore, a fluorescence quencher, or a combination thereof.

In a preferred embodiment, the present invention provides a method wherein the probe nucleic acid sequence consists of X-SEQ ID NO:10-Y or X-SEQ ID NO:11-Y, wherein X is a fluorophore, and wherein Y is a dark quencher or acceptor dye.

In a preferred embodiment, the present invention provides a method wherein the sample is a biological sample obtained from a subject, preferably whole blood.

In a preferred embodiment, the present invention provides a method that discriminates between *S. pneumoniae* nucleic acid and a pneumococcus-like viridans Streptococci (P-LVS) nucleic acid.

In a second aspect, the present invention provides a method for diagnosing a *S. pneumoniae* infection in a subject suspected of having a *S. pneumoniae* infection comprising the steps of obtaining a sample comprising nucleic acids from the subject; contacting the sample with one or more nucleic acid probes, wherein the probe nucleic acid sequence consists of X-SEQ ID NO:10-Y or X-SEQ ID NO:11-Y, wherein X is a fluorophore, and wherein Y is a dark quencher or acceptor dye; amplifying a *S. pneumoniae* ribonucleic acid with a set of primers comprising one or more forward primers consisting essentially of the nucleic acid sequence set forth as SEQ ID NO: 1 or SEQ ID NO: 3 and one or more reverse primers consisting essentially of the nucleic acid sequence set forth as SEQ ID NO: 2 or SEQ ID NO: 4; wherein the set of primers is capable of hybridizing to and directing the amplification of said *S. pneumoniae* ribonucleic acid; and detecting hybridization between the *S. pneumoniae* ribonucleic acid sequence present in the sample and the probe, wherein the detection of hybridization indicates that the subject is infected with *Streptococcus pneumonia*.

In a third aspect, the present invention provides a set of primers for the amplification of a *S. pneumoniae* ribonucleic acid comprising one or more forward primers consisting essentially of the nucleic acid sequence set forth as SEQ ID NO: 1 or SEQ ID NO: 3; and one or more reverse primers consisting essentially of the nucleic acid sequence set forth as SEQ ID NO: 2 or SEQ ID NO: 4 wherein the set of primers is capable of hybridizing to and directing the amplification of the *S. pneumoniae* ribonucleic acid.

In a preferred embodiment, the set of primers is provided for use in a method according to the present invention.

In a third aspect, the present invention provides a kit for detecting a *S. pneumoniae* ribonucleic acid in a sample, comprising a probe which nucleic acid sequence consists of X-SEQ ID NO:10-Y or X-SEQ ID NO:11-Y, wherein X is a fluorophore, and wherein Y is a dark quencher or acceptor dye; and a set of primers comprising one or more forward primers consisting essentially of the nucleic acid sequence set forth as SEQ ID NO: 1 or SEQ ID NO: 3 and one or more reverse primers consisting essentially of the nucleic acid sequence set forth as SEQ ID NO: 2 or SEQ ID NO: 4, wherein the set of primers is capable of hybridizing to and directing the amplification of the *S. pneumoniae* ribonucleic acid.

In a preferred embodiment, the kit is provided for use in a method according to the present invention.

The advantage of the present invention resides in the fact that the starting material is the RNA which is specific to the dividing bacteria; which reduces the chances of false positive results.

DESCRIPTION OF THE FIGURES

FIG. 1: Standard curve. Y-axis: $C_T$ values. X-axis: log concentrations of *S. pneumoniae* per ml of blood. E is the QPCR efficiency. $R^2$ is the coefficient of determination of the linear regression line.

DETAILED DESCRIPTION OF THE INVENTION

The present invention relates to a method, a set of primers and a kit for detecting a *S. pneumoniae* ribonucleic acid in a sample.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

Definitions

In the present application, terms are utilized for which the definitions are given as a preamble below. Technical terms are used according to conventional usage. To facilitate review of the various embodiments of the invention, the following explanations of terms are provided:

Animal: A living multi-cellular vertebrate or invertebrate organism, a category that includes, for example, mammals and birds. The term mammal includes both human and non-human mammals. Similarly, the term "subject" includes both human and veterinary subjects. Preferably, the subject is a human.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, for example the number of copies of a S. pneumoniae nucleic acid, such as a S. pneumoniae lytA nucleic acid or fragment thereof. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR; real-time reverse transcriptase PCR (it RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA, for example an RNA from S. pneumoniae, such as an RNA encoding S. pneumoniae lytA, psaA, or ply.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G).

Flap sequence: primers portion that are non-complementary to the target, also called overhang or tail.

Probe: A probe comprises an isolated nucleic acid capable of hybridizing to a target nucleic acid (such as a S. pneumoniae nucleic acid, for example a S. pneumoniae lytA, psaA, or ply nucleic acid molecule). A detectable label or reporter molecule can be attached to a probe. Typical labels include radioactive isotopes, enzyme substrates, co-factors, ligands, chemiluminescent or fluorescent agents, haptens, and enzymes.

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Quantitating a nucleic acid molecule: Determining or measuring a quantity (such as a relative quantity) of nucleic acid molecules present, such as the number of amplicons or the number of nucleic acid molecules present in a sample. In particular examples, it is determining the relative amount or actual number of nucleic acid molecules present in a sample, such as S. pneumoniae nucleic acid molecules present in a sample.

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a S. pneumoniae nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999) and to PCR Protocols (Academic Press New York, 1989).

In some examples, the amount of amplified target nucleic acid (such as a *S. pneumoniae* nucleic acid molecule for example a *S. pneumoniae* lytA, psaA, or ply nucleic acid molecule) is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification (such as *S. pneumoniae* nucleic acid amplification).

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as a *S. pneumoniae* nucleic acid molecule, such as a *S. pneumoniae* lytA, a psaA, or a ply nucleic acid molecule.

Detect: To determine if an agent (such as a signal, particular nucleotide, amino acid, nucleic acid molecule, and/or organism) is present or absent, for example *S. pneumoniae*. In some examples, this can further include quantification. For example, use of the disclosed probes in particular examples permits detection of a fluorophore, for example, detection of a signal from a fluorophore, which can be used to determine if a nucleic acid corresponding to nucleic acid of *S. pneumoniae* (such as a *S. pneumoniae* lytA nucleic acid molecule, a *S. pneumoniae* psaA nucleic acid molecule, or a *S. pneumoniae* ply nucleic acid molecule) is present. The detection of a *S. pneumoniae* nucleic acid molecule indicates the presence of *S. pneumoniae* in the sample, for example a *S. pneumoniae* infection in the sample.

Fluorophore: A chemical compound, which when excited by exposure to a particular stimulus such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the *S. pneumoniae* specific probes and primers disclosed herein are known to those of skill in the art and include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]na[rho]hthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfiuorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; 5 Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetrame[Lambda]yl-6-carboxyrhodarnine (TAMRA), tetramethyl rhodamine, and tetramethyl rhodamine isothiocyanate 10 (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and CyS[omicron]-carboxyfluorescein; boron dipyrromethene difluoride (BODIPY); acridine; stilbene; 6-carboxy-X-rhodamine (ROX); Texas Red; Cy3; Cy5, VIC® (Applied Biosystems); LC Red 640; LC Red 15 705; and Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

"Acceptor fluorophores" are fluorophores which absorb energy fiom a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a 25 fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 ran. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 A. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Forster radius, whereas if the donor fluoresces at its characteristic wavelength, it denotes that the distance between the donor and acceptor molecules has increased beyond the Forster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes, such as HybProbes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99%, such as 100% sequence identity to any of SEQ ID NOs:1-11 are provided herein. One of skill in the art will appreciate that these sequence identity ranges are provided for guidance only; it is possible that probes and primer can be used that fall outside these ranges.

Whole blood comprises red blood cells also called erythrocytes, white blood cells also called leucocytes and platelets.

Embodiments of the Invention

In a first aspect, the present invention provides a method for detecting the presence of a bacterial nucleic acid in a given sample. Ina preferred embodiment, the present invention provides a method for detecting S. pneumoniae nucleic acid in a sample, comprising the steps of:—isolating said nucleic acid and—detecting hybridization between the S. pneumoniae nucleic acid and a labeled probe, wherein the detection of hybridization comprises detecting a change in signal from the labeled probe during or after hybridization relative to the labeled probe signal before hybridization. The method is characterized in that said nucleic acid is a ribonucleic acid, which isolation comprises the addition of acidic phenol to said sample and the purification of said ribonucleic acid.

In a preferred embodiment, detecting the presence of a S. pneumoniae nucleic acid sequence in a sample includes the extraction of S. pneumoniae RNA. RNA extraction relates to releasing RNA from a latent or inaccessible form in a cell or sample and allowing the RNA to become freely available. In such a state, it is suitable for effective detection and/or amplification of the S. pneumoniae nucleic acid. Releasing RNA may include steps that achieve the disruption of cells. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular components, wherein such components may be either particulate or dissolved.

In a preferred embodiment of the present invention, RNA is isolated by homogenizing the cells of the collected sample in guanidinium thiocyanate and the RNA is purified from the lysate by extraction with acidic phenol at reduced pH. Said pH is comprised between 0 and 7, preferably between 1 and 6, more preferably between 2 and 5, most preferably around 4.

In another preferred embodiment of the present invention, RNA is isolated by homogenizing the cells of the collected sample in guanidinium thiocyanate and the RNA is purified from the lysate by extraction with phenol-chlorophorm at reduced pH. Said pH is comprised between 0 and 7, preferably between 1 and 6, more preferably between 2 and 5, most preferably around 4.

In a preferred embodiment of the present invention, RNA is isolated by adding heated acidic phenol to the sample. Preferably acidic phenol temperature is comprised between 45 and 85° C., more preferably between 55 and 75° C., most preferably around 65° C. The volume of added acidic phenol is comprised between 0.5 and 2.5 the volume of the sample, preferably the volume of acidic phenol added is equal to the volume of the sample. The mixture of the sample and the acidic phenol is then mixed for 3 to 10 min, preferably for 4 to 8 min, more preferably for about 5 min at a temperature comprised between 45 and 85° C., more preferably between 55 and 75° C., most preferably around 65° C. The mixture is then centrifuged for about 20 min at a speed about 14.000 g at a temperature comprised between 2 and 6° C., preferably between 3 and 5° C., more preferably about 4° C. Afterwards the supernatant is collected.

In a preferred embodiment, the volume of collected supernatant is smaller than the volume of supernatant obtained after centrifugation. This leads to the reduction of false positive and negative results due to the fact that the chance of collecting molecules other than RNA is smaller.

In a further preferred embodiment, the RNA is purified from the obtained supernatant using a commercial kit selected from the group of RNeasy midi kit (Qiagen), PureLink™ Pro 96 RNA Purification Kit (Invitrogen), GeneJET RNA Purification Kit (Fermentas) and RNA Clean & Concentrator™-5 (Zymo research).

In a preferred embodiment of the present invention, unspecific cDNA is produced from the isolated RNA by using random primers and retrotranscriptase. Commercial kits such as but not limited to the GoScript Reverse Transcription System (promega), the Super Script III (Invitrogen) and the I-Script (Biorad) can be used for cDNA production. The produced cDNA can be used for molecular typing. Indeed, specific serotypes sequences will be used as targets in order to perform molecular typing of the capsule of S. pneumonia.

In a preferred embodiment, the S. pneumoniae nucleic acid cDNA, is detected in real-time, for example by real-time PCR, in order to determine the presence, and/or the amount of S. pneumoniae specific nucleic acid in a sample. In this manner, an amplified nucleic acid sequence, such as an amplified S. pneumoniae wzg or ply nucleic acid sequence can be detected using a probe specific for the product amplified from the S. pneumoniae sequence of interest. S. pneumoniae wzg nucleic acid encodes capsular proteins and Ply nucleic sequence encodes the pneumococcal virulence factor pneumolysin.

In a preferred embodiment, the amplification of S. pneumoniae nucleic acid involves contacting the S. pneumoniae nucleic acid with one or more primers that are capable of hybridizing to and directing the amplification of a S. pneumoniae nucleic acid. In a further preferred embodiment, said one or more primers are capable of hybridizing under very high stringency conditions to a S. pneumoniae nucleic acid sequence.

In a preferred embodiment, the sample is contacted with a pair of primers that include a forward and reverse primer that both hybridize to a S. pneumoniae ply and/or wzg nucleic acid.

In a preferred embodiment, the present invention provides a method wherein said at least one primer have a length comprised between 10 and 60, preferably between 12 and 50, more preferably between 15 and 40 nucleotides capable of hybridizing under high, preferably under very high stringency conditions to a S. pneumoniae ribonucleic acid.

In a further preferred embodiment, the primer comprises a nucleic acid sequence at least 90%, preferably 95%, more preferably 100% identical to the nucleotide sequence set forth as SEQ ID NO: 1, SEQ ID NO: 2, SEQ ID NO: 3 or SEQ ID NO: 4.

In a preferred embodiment of the present invention, said at least one primer comprises at least one flap sequence, which is at least 90%, preferably 95%, more preferably 100% identical to the nucleotide sequence set forth as SEQ ID NO: 5.

Detecting a S. pneumoniae nucleic acid in a sample involves contacting the sample with at least one of the S. pneumoniae specific probes disclosed herein that is capable of hybridizing to a S. pneumoniae nucleic acid, such as a S. pneumoniae ply nucleic acid or S. pneumoniae wzg nucleic acid under conditions of very high stringency.

Detection of hybridization between the probe and the S. pneumoniae nucleic acid indicates the presence of the S. pneumoniae nucleic acid in the sample, for example detection of hybridization between the S. pneumoniae wzg probe and the S. pneumoniae wzg nucleic acid indicates the presence of the S. pneumoniae nucleic acid in the sample and detection of hybridization between the S. pneumoniae ply probe and the S. pneumoniae ply nucleic acid indicates the presence of the S. pneumoniae nucleic acid in the sample.

In one embodiment, the detection of a target nucleic acid sequence of interest, such as a S. pneumoniae lytA nucleic acid, a S. pneumoniae psaA nucleic acid, or a S. pneumoniae ply nucleic acid, includes the combined use of PCR amplification and a labeled probe such that the product is measured using real-time PCR.

In one embodiment, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes or between a fluorophore and a non-fluorescent quencher on the same probe (for example, using a molecular beacon or a TAQMAN® probe) can identify a probe that specifically hybridizes to the DNA sequence of interest and in this way, using a S. pneumoniae wzg probe and/or a S. pneumoniae ply probe, can detect the presence, and/or determine the amount of S. pneumoniae in a sample. In some embodiments, the fluorescently-labeled DNA probes used to identify amplification products have spectrally distinct emission wavelengths, thus allowing them to be distinguished within the same reaction tube, for example in multiplex PCR, for example a multiplex real-time PCR. In some embodiments, the probes and primers disclosed herein are used in multiplex real-time PCR. For example, multiplex PCR permits the simultaneous detection of the amplification products of a wzg and ply nucleic acid using the disclosed probes. Using the disclosed primers and probes, any combination of wzg and ply can be detected.

In another preferred embodiment, the present invention provides a method wherein the labeled probe is radiolabeled, fluorescently-labeled, biotin-labeled, enzymatically-labeled, or chemically-labeled.

In another preferred embodiment, the probe is labeled with a fluorophore, a fluorescence quencher, or a combination thereof. In a further preferred embodiment, probe nucleic acid sequence consists of X-SEQ ID NO:10-Y or X-SEQ ID NO:11-Y, wherein X is a fluorophore, and wherein Y is a dark quencher or acceptor dye.

In another preferred embodiment, the present invention provides a probe. In a further preferred embodiment said probe have a nucleic acid sequence that is at least 90%, preferably 95%, more preferably 100% identical to the nucleic sequence set forth in SEQ ID NO:10 or SEQ ID NO:11. In even further preferred embodiment, said probe have a nucleic acid sequence consisting of X-SEQ ID NO:10-Y or X-SEQ ID NO:11-Y, wherein X is a fluorophore, and wherein Y is a dark quencher or acceptor dye.

In another embodiment, a melting curve analysis of the amplified target nucleic acid can be performed subsequent to the amplification process. The melting temperature (Tm) of a nucleic acid sequence depends on the length of the sequence and its G/C content. Thus, the identification of the Tm for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR-green or ethidium bromide). SYBR green is a fluorogenic minor groove binding dye that exhibits little fluorescence when in solution but emits a strong fluorescent signal upon binding to double-stranded DNA.

An application of the S. pneumoniae specific primers and probes disclosed herein is the detection of S. pneumoniae in a sample, such as a biological sample obtained from a subject that has or is suspected of having an S. pneumoniae infection. Thus, the disclosed methods can be used to diagnose if a subject has a S. pneumoniae. In a preferred embodiment, said methods discriminate between S. pneumoniae nucleic acid and a pneumococcus-like viridans Streptococci (P-LVS) nucleic acid. This is due to the targeting of the wzg by the primers and the methods of the present invention. The wzg is highly specific to S. pneumoniae and does not lead to the detection of pneumococcus-like viridans Streptococci (P-LVS).

The methods described herein may be used for any purpose for which detection of S. pneumoniae is desirable, including diagnostic and prognostic applications, such as in laboratory and clinical settings. Appropriate samples include any conventional environmental or biological samples, including clinical samples obtained from a human or veterinary subject. Suitable samples include all biological samples useful for detection of bacterial infection in subjects, including, but not limited to, cells, tissues (for example, lung, liver and kidney), bone marrow aspirates, bodily fluids (for example, blood, serum, urine, cerebrospinal fluid, bronchoalveolar levage, tracheal aspirates, sputum, nasopharyngeal aspirates, oropharyngeal aspirates, saliva), eye swabs, cervical swabs, vaginal swabs, rectal swabs, stool, and stool suspensions. Other suitable samples include samples obtained from middle ear fluids, bronchoalveolar levage, tracheal aspirates, sputum, nasopharyngeal aspirates, oropharyngeal aspirates, or saliva. Preferably the sample is whole blood of a subject.

In a second aspect, the present invention provides a method for diagnosing a S. pneumoniae infection in a subject suspected of having a S. pneumoniae infection comprising the steps of obtaining a sample comprising nucleic acids from the subject; contacting the sample with one or more nucleic acid probes, wherein the probe nucleic acid sequence consists of X-SEQ ID NO:10-Y or X-SEQ ID NO:11-Y, wherein X is a fluorophore, and wherein Y is a dark quencher or acceptor dye; amplifying a S. pneumoniae ribonucleic acid with a set of primers comprising one or more forward primers consisting essentially of the nucleic acid sequence set forth as SEQ ID NO: 1 or SEQ ID NO: 3 and one or more reverse primers consisting essentially of the nucleic acid sequence set forth as SEQ ID NO: 2 or SEQ ID NO: 4; wherein the set of primers is capable of hybridizing to and directing the amplification of said S. pneumoniae ribonucleic acid; and detecting hybridization between the S. pneumoniae ribonucleic acid sequence present in the sample and the probe, wherein the detection of hybridization indicates that the subject is infected with Streptococcus pneumonia.

In another preferred embodiment, the present invention provides a method wherein multiplex RT-PCR reactions are used in order to amplify at least two different nucleic acid sequences of S. pneumonia. In a preferred embodiment, a mixture of primers and/or probes is used in said multiplex reactions. Preferably the mixture of primers and/or probes is selected from table 1.

In a third aspect, the present invention provides a set of primers for the amplification of a S. pneumoniae ribonucleic acid comprising one or more forward primers consisting essentially of the nucleic acid sequence set forth as SEQ ID NO: 1 or SEQ ID NO: 3; and one or more reverse primers consisting essentially of the nucleic acid sequence set forth as SEQ ID NO: 2 or SEQ ID NO: 4 wherein the set of primers is capable of hybridizing to and directing the amplification of the S. pneumoniae ribonucleic acid.

In a preferred embodiment, the set of primers is provided for use in a method according to the present invention.

In a third aspect, the present invention provides a kit for detecting a S. pneumoniae ribonucleic acid in a sample, comprising a probe which nucleic acid sequence consists of X-SEQ ID NO:10-Y or X-SEQ ID NO:11-Y, wherein X is a fluorophore, and wherein Y is a dark quencher or acceptor dye; and a set of primers comprising one or more forward primers consisting essentially of the nucleic acid sequence set forth as SEQ ID NO: 1 or SEQ ID NO: 3 and one or more reverse primers consisting essentially of the nucleic acid sequence set forth as SEQ ID NO: 2 or SEQ ID NO: 4, wherein the set of primers is capable of hybridizing to and directing the amplification of the S. pneumoniae ribonucleic acid. A nucleic acid probe and/or primer may be provided suspended in an aqueous solution or as a freeze-dried or lyophilized powder, for instance.

In a preferred embodiment, the kit also may include the reagents necessary to carry out amplification reactions, including DNA sample preparation reagents, appropriate buffers (such as polymerase buffer), salts (for example, magnesium chloride), and deoxyribonucleotides (dNTPs). One or more control sequences for use in the PCR reactions also may be supplied in the kit (for example, for the detection of human RNAse P). The kit further comprises instructions including directions for obtaining a sample, processing the sample, preparing the probes, and/or contacting each probe with an aliquot of the sample.

In a preferred embodiment, the kit is provided for use in a method according to the present invention.

The preferred embodiments of the invention described herein are not intended to limit the scope of the invention, since these embodiments are illustrations of several preferred aspects of the invention. Any equivalent embodiments are intended to be within the true spirit and scope of this invention. Indeed, various modifications of the invention in addition to those shown and described herein will become apparent to those skilled in the art from the preceding detailed description. Such modifications are also intended to fall within the scope of the appended claims.

The advantage of the present invention resides in the fact that the starting material is the RNA which is specific to the dividing bacteria; which reduces the chances of false positive results. Indeed, the method according to the present invention allows the detection of less than 50 bacteria per ml of blood.

EXAMPLES

It is extremely important that all experiments are conducted in a highly sterile environment and using sterile material. The user should always wear laboratory gloves.

Example 1: Blood Contamination Using a S. pneumoniae Culture in Stationary Phase and Contaminated Blood Using a S. pneumoniae Culture in Exponential Phase S. pneumonia serotype 1 (code 070799) was cultured in exponential and in stationary phase. Culture technique of S. pneumonia is known for the person skilled in the art. From each culture, $10^{-1}$, $10^{-2}$, $10^{-3}$, $10^{-4}$, $10^{-5}$ and $10^{-6}$ dilutions were prepared in Todd Hewitt Broth medium.

Whole blood samples were collected from voluntary humans into collection tubes containing $EDTAK_2$ anticoagulant. Aliquots were generated from the collected samples such as each aliquot contained 2 ml of blood. The aliquots were then contaminated by the different dilutions of S. pneumonia cultured in exponential and in stationary phase. The contaminated samples were then frozen at −80° C.

Example 2: Total RNA Extraction and Purification

Contaminated blood samples were defrosted by placing them in a mixture of ice and water for a period of 90 minutes. Afterwards, an equal volume of heated acidic phenol was added to each sample. The mixture of the sample and the acidic phenol was then mixed about 5 min at 65° C. The mixture was then centrifuges 20 min at 14.000 g at 4° C. 500 µl of the supernatant were then collected. RNA was purified from the obtained supernatant using the RNeasy midi kit of Qiagen according to the manufacturer's instructions. The purity of the isolated RNA was then monitored using spectrophotometric measurements.

Example 3: cDNA Production

10 µl of the purified DNA are mixed with 1 µl of the random primers. Secondary structures are then denaturated in a thermocycler for 5 min at 70° C. Afterwards, 14 µl of mastermix is added and retro transcription is performed for 10 min at 25° C. followed by a cycle of 60 min at 50° C. The Go script reverse Transcriptase® of Promega was used for retro-transcription of the purified RNA.

Example 4: Real Time PCR Detection and Amplification of wzg and ply Genes

Primers

Specific primers for the wzg and the ply genes of *S. pneumonia* were designed. The primer sequences are listed in table 1. The primers were synthetized with a flap sequence at their 5' end. The sequence of the flap sequence is given in table 1. The primers were also purified in HPLC.

Taqman® Real Time PCR

The primers and the probe were used at a concentration equal to 12.5 µM. These diluted primers and probes are used to prepare the master mix of the reaction.

To amplify the wzg gene the master mix is obtained by mixing 2 µl of the wzg forward primer and the wzg reverse primer with 2 µl of the wzg probe, 9 µl of sterile water and 25 µl of IQ-Mix 2×.

To amplify the ply gene the master mix is obtained by mixing 2 µl of the ply forward primer and the ply reverse primer with 2 µl of the ply probe, 9 µl of sterile water and 25 µl of IQ-Mix 2×.

20 µl of the prepared cDNA is added to each mix and the real time PCR reactions were carried out starting with incubation at 95° C. for 3 min, followed by 45 cycles of 95° C. for 10 seconds and 60° C. for 30 seconds. Reactions were carried out in triplicate. A positive and a negative sample were also included in our experiment.

The threshold ($C_T$) data was determined using default threshold settings. The $C_T$ cycle is defined as the fractional cycle number at which the fluorescence passes the fixed threshold. From the tested samples, a standard curve was obtained with an $R^2$ value of 0.972 (see figure with the experiment). This showed the reproducibility of our method.

We also performed an in silico analysis which showed that the targeted gene (wzg) is highly specific to *S. pneumoniae* and does not lead to the detection of pneumococcus-like viridans Streptococci (P-LVS).

Example 5: Detection of *S; pneumoniae* Presence in Clinical Samples

Whole blood samples were collected from different humans having pneumonia (20 samples) and from healthy humans (10 samples). Each sample was treated as described in examples 2, 3 and 4 for such respectively, RNA was extracted, cDNA was produced and *S. pneumonia* genes presence was detected. Our results experiments did not lead to any false positive as the samples collected from the healthy humans did not give any signal after RT-PCR (results not shown). The samples collected from sick humans showed an amplification signal during RT-PCR. The obtained RT-PCR results were used together with the standard curve to determine the concentration of *S. pneumonia* nucleic acid in the tested samples. The obtained preliminary data have shown that the experiment gave very good results with clinical samples.

TABLE 1 nucleic sequence of the primers, probes and flap sequence

| Primers | Primer sequences |
|---|---|
| SEQ ID NO 1: WZG Forward | 5' ACGTCTAAGAATCAGTCTTTC 3' |
| SEQ ID NO 2: WZG Reverse | 5' CGACACCGAACTAATAGG 3' |
| SEQ ID NO 3: Ply Forward | 5' TAACAGCTACCAACGACAG 3' |
| SEQ ID NO 4: Ply Reverse | 5' GCAAGAAGAGTGGGATTATTC 3' |
| SEQ ID NO 5: Flap | 5' AATAAATCATAA 3' |
| SE|Q ID NO 6: WZG with Flap Forward | 5' AATAAATCATAA-ACGTCTAAGAATCAGTCTTTC 3' |
| SEQ ID NO 7: WZG with Flap Reverse | 5' AATAAATCATAACGACACCGAACTAATAGG 3' |
| SEQ ID NO 8: Ply with Flap Forward | 5' AATAAATCATAATAACAGCTACCAACGACAG 3' |
| SEQ ID NO 9: Ply with Flap Reverse | 5' AATAAATCATAAGCAAGAAGAGTGGGATTATTC 3' |
| SEQ ID NO 10: Probe WZG | 5' HEX-CCATAGGTGTCAATTCCAC-BHQ1 3' |
| SEQ ID NO 11: Probe Ply | 5' FAM-AAGGTCTCATCCACTACGA-BHQ1 3' |
| SEQ ID NO 12: lytA forward | 5' CCATCTGGCTCTACTGTG 3' |
| SEQ ID NO 13: lytA Reverse | 5' GGAACAGGCTGGTACTAC 3' |

TABLE 1-continued nucleic sequence of the primers, probes and flap sequence

| Primers | Primer sequences |
|---|---|
| SEQ ID NO 14: lytA with Flap Forward | 5' AATAAATCATAACCATCTGGCTCTACTGTG 3' |
| SEQ ID NO 15: lytA with Flap Reverse | 5' AATAAATCATAAGGAACAGGCTGGTACTAC 3' |
| SEQ ID NO 16: Probe lytA | 5' Texas Red-TGCCAGTGTTCCGTCT-BHQ2 3' |

---

What is claimed is:

1. A method for detecting *Streptococcus pneumoniae* (*S. pneumoniae*) ribonucleic acid in a sample, comprising the steps of:
isolating said ribonucleic acid, wherein said isolation comprises adding acidic phenol to said sample and purifying said ribonucleic acid,
synthesizing a deoxyribonucleic acid from the isolated ribonucleic acid,
contacting said deoxyribonucleic acid with at least two primers, each primers comprising at least one flap sequence, wherein a first primer sequence is identical to the nucleotide sequence set forth as SEQ ID NO: 6 and a second primer sequence is identical to the nucleotide sequence set forth as SEQ ID NO: 7,
contacting said deoxyribonucleic acid with at least one labeled probe having a nucleic acid sequence consisting of X-SEQ ID NO:10-Y, wherein X is a fluorophore, and Y is a dark quencher or acceptor dye,
amplifying the *S. pneumoniae* deoxyribonucleic acid by real-time PCR, and
detecting hybridization between the *S. pneumoniae* nucleic acid and said labeled probe, wherein the detection of hybridization comprises detecting a change in signal from the labeled probe during or after hybridization relative to the labeled probe signal before hybridization.

2. The method according to claim 1, wherein the sample is a biological sample obtained from a human or veterinary subject, selected from the group consisting of cells, tissues, bone marrow aspirates, bodily fluids, eye swabs, cervical swabs, vaginal swabs, rectal swabs, stool, stool suspensions, samples obtained from middle ear fluids, bronchoalveolar lavage, tracheal aspirates, sputum, nasopharyngeal aspirates, oropharyngeal aspirates and saliva.

3. The method according to claim 1, wherein a *S. pneumonia* wzg ribonucleic acid is targeted using a forward primer comprising the nucleic acid sequence identical to the nucleotide sequence set forth as SEQ ID NO: 6 and a reverse primer comprising the nucleic acid sequence identical to the nucleotide sequence set forth as SEQ ID NO: 7, thereby discriminating between *S. pneumoniae* nucleic acid and a pneumococcus-like viridans Streptococci (P-LVS) nucleic acid.

4. A method for diagnosing a *S. pneumoniae* infection in a subject suspected of having a *S. pneumoniae* infection comprising the steps of:
obtaining a sample comprising nucleic acids from the subject,
isolating a ribonucleic acid from the sample, wherein said isolation comprises adding acidic phenol to said sample and purifying said ribonucleic acid,
synthesizing a deoxyribonucleic acid from the isolated ribonucleic acid,
contacting the sample with one or more nucleic acid probes, wherein the probe nucleic acid sequence consists of X-SEQ ID NO:10-Y, wherein X is a fluorophore, and wherein Y is a dark quencher or acceptor dye,
amplifying a *S. pneumoniae* ribonucleic acid with a set of primers comprising a forward primer consisting essentially of the nucleic acid sequence set forth as SEQ ID NO: 6 and a reverse primer consisting essentially of the nucleic acid sequence set forth as SEQ ID NO: 7; wherein the set of primers is capable of hybridizing to and directing the amplification of said *S. pneumoniae* ribonucleic acid, and
detecting hybridization between the *S. pneumoniae* ribonucleic acid sequence present in the sample and the probe, wherein the detection of hybridization indicates that the subject is infected with *Streptococcus pneumonia*.

5. The method according to claim 1, wherein the labeled probe and the at least two primers are part of a kit for detecting a *S. pneumoniae* ribonucleic acid in a sample wherein the kit comprises:
a probe which nucleic acid sequence consists of X-SEQ ID NO:10-Y, wherein X is a fluorophore, and wherein Y is a dark quencher or acceptor dye,
a set of primers comprising one or more forward primers consisting essentially of the nucleic acid sequence set forth as SEQ ID NO: 6 and one or more reverse primers consisting essentially of the nucleic acid sequence set forth as SEQ ID NO: 7, wherein the set of primers is capable of hybridizing to and directing the amplification of the *S. pneumoniae* ribonucleic acid.

6. The method according to claim 1, wherein the sample is whole blood from a human or veterinary subject.

* * * * *